United States Patent [19]

Kern

[11] Patent Number: 4,752,617

[45] Date of Patent: Jun. 21, 1988

[54] ANTI-BACTERIAL METHODS AND AGENTS

[75] Inventor: Gerald N. Kern, 4631 Louise Ave., Encino, Calif. 91316

[73] Assignee: Gerald N. Kern, Encino, Calif.

[21] Appl. No.: 98,046

[22] Filed: Sep. 16, 1987

Related U.S. Application Data

[62] Division of Ser. No. 741,681, Jun. 5, 1985, Pat. No. 4,717,737.

[51] Int. Cl.$^4$ ............................................. A61K 7/48
[52] U.S. Cl. .................................... 514/547; 514/859
[58] Field of Search ................................ 514/547, 859

[56] References Cited

U.S. PATENT DOCUMENTS

| | | | |
|---|---|---|---|
| 2,028,091 | 1/1936 | Jaeger | 260/106 |
| 2,149,240 | 2/1939 | Crossley | 167/58 |
| 2,176,423 | 10/1939 | Jaeger | 260/481 |
| 2,574,526 | 11/1951 | Bordon et al. | 117/86 |
| 3,650,964 | 3/1972 | Sedliar et al. | 252/106 |
| 3,737,552 | 6/1973 | Gordon et al. | 424/313 |
| 3,873,721 | 3/1975 | Hargett | 424/313 |
| 3,942,512 | 3/1976 | Hargett | 128/1 |
| 3,984,570 | 10/1976 | Bent et al. | 424/390 |
| 4,013,418 | 3/1977 | Plakas | 23/253 |
| 4,066,786 | 1/1978 | Bent et al. | 424/313 |
| 4,096,311 | 6/1978 | Pietreniak | 428/289 |
| 4,146,470 | 3/1979 | Mohan et al. | 210/2 |
| 4,148,872 | 4/1979 | Wagenknecht et al. | 424/48 |
| 4,156,715 | 3/1979 | Wagenknecht et al. | 424/48 |
| 4,156,716 | 3/1979 | Wagenknecht et al. | 424/48 |
| 4,157,385 | 6/1979 | Wagenknecht et al. | 424/48 |
| 4,161,517 | 9/1979 | Wagenknecht et al. | 424/48 |
| 4,307,143 | 12/1981 | Meitner | 252/91 |
| 4,334,910 | 6/1982 | Lorimez et al. | 71/82 |
| 4,387,107 | 6/1983 | Klein et al. | 514/714 |
| 4,514,385 | 4/1985 | Damani et al. | 424/81 |
| 4,540,566 | 9/1985 | Davis et al. | 424/22 |
| 4,578,265 | 3/1986 | Pellico et al. | 424/50 |

FOREIGN PATENT DOCUMENTS

| | | |
|---|---|---|
| 0107594 | 5/1984 | European Pat. Off. . |
| 53-113019 | 10/1978 | Japan . |
| 56-15202 | 2/1981 | Japan . |
| 2103089 | 7/1982 | United Kingdom . |

OTHER PUBLICATIONS

A. G. Gilman, L. S. Goodman and A. Gilman, The Pharmacological Basis of Therapeutics (1980) Sixth Edition, pp. 1008–1009.
Department of Health and Human Services Food and Drug Administration, Report Docket No. 84N-0184. "Dioctyl Sodium Sulfosuccinate, Dioctyl Potassium Sulfosuccinate, and Dioctyl Calcium Sulfosuccinate;" Availability of the Final Report of the DSS Scientific Review Panel, Mar. 1984.
Article titled "Injury of Bacteria by Sanitizers", D. L. Scheusner et al., (Dept. Food Sci., North Carolina State University, Raleigh, N.C. (Appl. Microbiol. 1971, 21(1), 41–45.
Article titled "Bloat in Cattle. XVI. Development and Application of Techniques for Selecting Drugs to Prevent Feedlot Bloat", R. M. Meyer et al., (Kansas Agric. Exp. Stn. Kansas State Univ. Manhattan, Kans.) J. Admin. Sci. 1972, 34(2), 234–240.
Baker et al., "Action of Synthetic Detergents on the Metabolism of Bacteria" J. Exp. Med., 73 2490271, (1941).
Chemical Abstract (56:9226g) Belgian article titled "Bactericidal Properties of Anionic Detergents".
Article titled "Studies of the Anti-Microbial Activity of Nonionic and Anionic Surfactants", Chuichi Ishizeki, (Eisei Shikensho, Japan), Eisei Shikenjo Hokoku, 1970, (88), 75–78.
Accepted Dental Therapeutics, 35th Ed., published by the American Association, Chicago, 1973, p. 265.
"Effects of Antiviral Agents on the Potato Y Virus in Intact Potato Plants. II. Antimetabolites and Other Antiviral Substances" Hans Hect et al., (Bayer. Landesanst. Bodenkult, Pflanzenbau, Freising. Ger.), Bayer, Landsirtsch Jahrb. 1978, 55(4), 433–457.
"Spraying Potatoes to Prevent Leaf Roll Spread by the Green Peach Aphid", W. A. Shands et al., (Univ. Maine, Orono, Maine), Amer. Potato J. 1972, 49(1), 23–34.

(Continued on next page.)

Primary Examiner—Shep K. Rose
Attorney, Agent, or Firm—Christie, Parker & Hale

[57] ABSTRACT

Methods and compositions are provided for treating selected bacterial infections wherein the anti-bacterially active ingredient is a compound of the following formula:

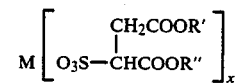

wherein R' and R" are each independently a straight chain or branched chain alkyl group having from 5 to 8 carbon atoms, M is $NH_4$, Na, K or Ca, and x is 1 when M is Na, K or $NH_4$, and x is 2 when M is Ca.

6 Claims, No Drawings

OTHER PUBLICATIONS

"Effects of Several Wetting Agents on the Viability of an Arthroaleuriosporous Fungus", G. F. Orr et al., (Environ, Life Sci. Div., U.S. Army Dugway Proving Ground, Dugway, Utah), Bulletin Torrey Botanical Club 1977, 104(1), 25–28.

"The Effect of Post-Infectional Potato Tuber Metabolites and Surfactants on Zoospores of Oomycetes", Jane E. Harris et al., (A.R.C. Food Res. Inst., Norwich, Engl.), Physiol. Plan Pathol., 1977, 11(2), 163–169.

"Eradication of the Perithecial Stage of Apple Scab with Surfactants", R. T. Burchill et al., (East Malling Res. Stn., Maidstone/Kent, Engl.), Ann. Appl. Biol. 1977, 87(2), 229–231.

"Effects of some Surfactant Fungicides on Rhizobium Trifolii and Its Symbiotic Relationship with White Clover", D. J. Fisher et al., (Long Ashton Res. Stn., Univ. Bristol, Long Ashton/Bristol, Engl.), Ann. Appl. Biol., 1978, 90(1), 73–84.

"Effects of Fungicides and Surfactants on the Zoospores of Olpidium Brassicae", J. A. Tomlinson et al., (Natl. Veg. Res. Stn., Wellesbourne/Warwick, Engl. CV 359EF), Ann. Appl. Biol. 1979, 93(1), 13–19.

"Surfactants for the Control of Apple Mildew", Derek R. Clifford et al., (Long Ashton Res. Stn., Univ. Bristol, Bristol, Engl.), Pestic. Sci. 1975, 6(4), 409–418.

"Surfactants as Fungicides", F. R. Forsyth, Canadian Journal of Botany 42, (1964), pp. 1335–1347.

"Greenhouse Evaluation of Chemicals for Control of Powdery Mildews", A. H. M. Kirby et al., Ann. of Appl. Biol. (1963), 52, pp. 45–54.

ANTI-BACTERIAL METHODS AND AGENTS

This is a division of Application Ser. No. 741,681, filed June 5, 1985, now U.S. Pat. No. 4,717,737.

FIELD OF THE INVENTION

The field of the invention relates to anti-bacterial methods and anti-bacterial compositions. More particularly, this invention relates to methods for treating bacterial infections in humans and animals, for inhibiting bacteria on surfaces and articles and for anti-bacterial compositions for carrying out the aforementioned methods. Such compositions can include lotions, creams, ointments, salves, powders, sprays, capsules, tablets, suppositories, suspensions and solutions.

BACKGROUND OF THE INVENTION

Although the development of vaccines has lead to a dramatic reduction in many bacterial diseases of man and animals, bacterial diseases remain a major problem.

Such diseases can be acquired through various routes, including the respiratory tract, the alimentary tract, the skin and the mucosa, by sexual transmission and congential transfer.

Bacterial infections involving the respiratory tract are generally acquired by inhalation or ingestion of microorganisms from the air or by direct or indirect contact with respiratory secretions. The skin and adjoining mucosal surfaces offer a natural barrier to invasion by pathogenic bacterial species. However, minor abrasions, insect bites, and traumatization by surgical procedures can break the host's natural barriers and permit colonization by transient as well as indigenous bacterial species.

Microorganisms are indigested daily, and most are destroyed either by enzymes or acids encountered in the stomach and intestinal tract and/or they are eliminated in the feces. The ingested bacterial pathogens that survive their route through the intestinal tract may give rise to a variety of diseases. Some ingested bacterial agents from contaminated food or water, for example, may remain localized in the intestinal tract giving rise to the typical symptoms of gastroenteritis, whereas others that infect the gastrointestinal tract may penetrate the epithelial barrier and invade the bloodstream and cause systemic infection.

Bacteria can be identified and classified in various ways, including the use of a test called the Gram stain. By the Gram stain test, bacteria are classified as either Gram ositive or Gram negative. The difference between Gram positive and Gram negative bacteria relates, at least in part, to the different cell wall structure in Gram positive bacteria as opposed to the cell wall structure of Gram negative bacteria.

Various specific treatments are available for treating infections caused by a specific genus and/or a specific species of bacteria. There is, however, a need in the art for a method for treating (and/or preventing) bacterial infection which uses an anti-bacterial agent that is safe and effective for internal administration in humans and animals while at the same time is effective for treating (and/or preventing) infections caused by a wide variety of Gram positive bacteria.

SUMMARY OF THE INVENTION

The present invention is directed to methods for treating and/or preventing bacterial infections of humans and animals. One embodiment of the present invention is directed to a method for treating such bacterial infections which comprises administering to a human or animal having a bacterial infection caused by a Gram positive bacterium a compound of the following formula:

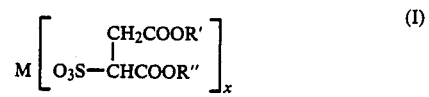

wherein R' and R" are each independently a straight chain or branched chain alkyl group having from 5 to 8 carbon atoms, M is a physiologically compatible group selected from $NH_4$, Na, K or Ca; x is 1 when M is $NH_4$, Na or K and x is 2 when M is Ca.

Another embodiment of the present invention is directed to methods for treating a superficial or cutaneous bacterial infection in animals or humans by topically applying to the external surface of the animal or human having a bacterial infection caused by a Gram positive bacteria a composition containing an effective anti-bacterial amount of a compound of the above Formula (I). By external surface of a human or animal is meant the skin, eye surfaces, fingernails and toenails and mucous membranes including, for example, the mouth, vagina and rectum.

In another embodiment of the present invention, the compound of Formula (I) is used in a method of disinfecting or sterilizing surfaces, such as kitchen, bathroom and hospital floors, walls, cabinets and counter tops, by spraying or wiping the surface with a solution containing an effective anti-bacterial concentration of a composition of the above Formula (I).

DETAILED DESCRIPTION

The anti-bacterial agent of the present invention is a compound of the following formula:

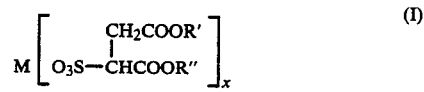

wherein R' and R" are each independently a straight chain or branched chain alkyl group having from 5 to 8 carbon atoms, M is a physiologically compatible group selected from $NH_4$, Na, K or Ca; x is 1 when M is $NH_4$, Na or K and x is 2 when M is Ca. The M group and the dosage of the compound of Formula (I) are selected such that the concentration of M in the human or animal host receiving the anti-bacterial agent will be at a nontoxic concentration in the host. Normally for systemic or local applications and for most topical applications, M will be Na, K and Ca.

The R' and R" groups can be the same or different. Preferably, however, R' and R" will be the same. Typical R' and R" groups include amyl, octyl and 2-ethylhexyl; preferably R' and R" are both 2-ethylhexyl. In the preferred embodiment of the present invention, M will be Na or Ca and most preferably M will be Na.

In the preferred embodiment of the present invention, the anti-bacterial agent of Formula (I) is dioctyl sodium sulfosuccinate [also known as 1,4-bis(2-ethylhexyl) sodium sulfosuccinate, docusate sodium, and DSS].

The effective dosage of the anti-bacterial agent is provided to the animal and human host in a delivery system which assures a systemic or local concentration of between about 0.01 and 0.2 mg of the anti-bacterial agent per ml of body fluids at the cellular level.

The term '37 systemic", as used herein with regard to concentration, means the concentration of the anti-bacterial agent per ml of body fluids at the cellular level within the body generally. The term "local", as used herein with regard to concentration, means the concentration of the anti-bacterial agent per ml of body fluids at the cellular level at a localized area within the body, for example, in a particular organ or other body site.

In accordance with the practice of the method of the present invention, bacterial infections in human or animal hosts caused by Gram positive bacteria including but not limited to Streptococcus, Staphylococcus, Actinomyces, *Arachnia propionica,* Bacillus, Bacterionema, Clostridium, Corynebacterium, *Coxiella burnetii, Erysipelothrix rhusiopathiae,* Eubacterium, Peptococcus, Mycobacterium, Nocardia, Peptostreptococcus, and Propionibacterium and the like are susceptible to treatment by administering to the host an effective anti-bacterial dosage of the above anti- bacterial agent. Although the method of this invention is described below with respect to dioctyl sodium sulfosuccinate, practice of principles of this invention is contemplated with the anti-bacterial agents of the above Formula (I) which are equivalent to dioctyl sodium sulfocuccinate, such as dioctyl calcium sulfosuccinate [1,4-bis(2-ethylhexyl) calciumsulfosuccinate] and dioctyl potassium sulfosuccinate [1,4-bis(2-ethylhexyl) potassium sulfosuccinate] and the like.

The term "treatment" or "treating" a bacterial infection as used herein, means administering an anti-bacterially effective amount of a compound of the above Formula (I) to a human or animal already infected. The term "preventing" a bacterial infection means administering an anti-bacterially effective amount of a compound of the above Formula (I) to a human or animal not already infected to thereby prevent infection. Administering an "anti-bacterially effective" amount of a composition of the above Formula (I) compound to a human or animal, as used herein, means administering a sufficient amount of such a compound to obtain a systemic, local or topical concentration of from about 0.01 to about 0.2 mg of the compound per ml of fluids at the cellular level.

Docusate sodium, which is a wax-like solid, is slowly soluble in water to a limited extent and is freely soluble in organic solvents such as alcohol. Docusate sodium can be prepared by esterification of maleic anhydride with 2-ethylhexyl alcohol followed by addition of sodium bisulfite. The other compounds of Formula (I) can be prepared by esterification of maleic anhydride with the appropriate physiologically acceptable alcohol followed by the addition of the appropriate bisulfite salt, such as ammonium bisulfite, potassium bisulfite, and calcium bisulfite.

Docusate sodium is widely used as a wetting agent in a variety of industrial, pharmaceutical, cosmetic and food additive applications. For example, it is used in cocoa preparations, evaporated milk, cold packed cheese food, cream cheese and french dressing as an additive. As a pharmaceutical it is used as a stool softening agent. To be effective as an anti-bacterial agent in accordance with the practice of the principles of the method of the present invention, the concentration of docusate sodium in the body fluids of the human and animal host at the cellular level must be at least about 0.01 mg of docusate sodium per ml of such fluid. This requires a dosage regimen of from about 5 mg to about 35 gms per day of docusate sodium in a delivery system which assures systemic or local concentration of at least about 0.01 mg of docusate sodium per ml of body fluids at the cellular level.

For systemic or local application, the concentration of docusate sodium in fluids at the cellular level is preferably no greater than about 0.2 mg per ml of such fluids to provide a safety factor thereby ensuring that there are not toxic side affects to the host. While docusate sodium is used as a food additive and as a pharmaceutical stool softening agent, it is known that such uses do not provide a systemic or local concentration of from about 0.01 mg to about 0.2 mg of docusate sodium per ml on a cellular level as is required for practice of the present invention.

Docusate sodium can be administered orally, intravenously, subcutaneously, intramuscularly, intracutaneously, topically or by inhalation or instillation into a body site or cavity. Regardless of the type of administration, it may be dispersed in a pharmaceutically acceptable carrier. For example, when administered orally, it can be in tablet or capsule carriers, which can include components such as excipients, bulking agents, lubricants, disintegrants, solubilizing solvents, dyes and the like. It can also be administered orally in a suitable liquid carrier. For example, a carrier comprising ethanol and/or glycerol or the like. The term "carrier" further includes vehicles or materials useful in preparing an injection or intravenous form of docusate sodium such as isotonic saline-type solutions, isotonic dextrose-type solutions and the like. When used topically to treat superficial and cutaneous bacterial infection it may be formulated into a pharmaceutically acceptable composition, such as, for example, a lotion, cream, solution emulsion, salve and the like. It can also be applied topically as a powder or dry or liquid spray. Additionally, it can be provided for administration in pharmaceutically acceptable mouthwash formulations for treating and/or preventing oral and laryngeal bacterial infections and for inhibiting dental plaque.

In further examples of vehicles for administration of docusate sodium, it may be provided in a pharmaceutically acceptable carrier for use as an aerosol spray for bronchial inhalation therapy, for instance. It may also be provided as the active anti-bacterial ingredient in an anti-bacterially effective powder. It may also be provided in a cleanser formulation for use in disinfecting body surfaces or as a sanitizer for disinfecting surfaces such as bathroom and kitchen fixtures and the like.

In a further exemplary embodiment of using docusate sodium as an anti-bacterial agent, a material such as a cellulosic web, can be used as a substrate or carrier for an effective amount of docusate sodium. Thus, for example, a facial tissue, a bathroom tissue or a hand towel or the like may be impregnated with an anti-bacterially effective amount of docusate sodium. Use of such impregnated tissues or towels can result in controlling spread of bacterial infection.

For example, non-woven substrates such as wet-creped hand towels and spunbonded and meltflown polymeric webs commonly used in disposable hospital items such as surgical drapes, gowns, bedsheets, pillow cases and textile materials and the like can be impregnated with docusate sodium. Hygienic face masks used by persons suffering from respiratory illness or by persons working in a dusty environment where the dust is contaminated with pathogenic bacteria can be impregnated with an anti-bacterially effective amount of docusate sodium. Further, disposable diapers can be impregnated with docusate sodium as well as tampons and intravaginal sponges and the like. Docusate sodium may also be provided in an appropriate carrier as a vaginal douche.

In one exemplary embodiment of the present invention, docusate sodium is provided in a time/sustained-release capsule form as is known in the art. In such form, from about 5 mg to about 35 gms of docusate sodium is administered per day to the human or animal host either as a treatment for an existing bacterial infection or as a prophylactic to prevent bacterial infection.

When docusate sodium is administered as a treatment for systemic or local bacterial infection, the dosage regimen is adjusted such that the systemic or local concentration of docusate sodium in the body fluids of the human or animal host at the cellular level is from about 0.01 to about 0.2 mg per ml of fluid. The treatment is continued until the infection is healed. When docusate sodium is administered as treatment for superficial and cutaneous bacterial infection, docusate sodium may be topically administered to bacterial lesions at the site of infection on the external surface of the human or animal host, preferably at least daily, until the infection is healed. For some superficial and cutaneous bacterial infections, topical treatment is augmented with systemic treatment as is described herein for treatment of systemic bacterial infections.

For the treatment of systemic bacterial infection and subcutaneous bacterial infection, the preferred method of treatment is internal administration of docusate sodium to effect a systemic or local concentration of from about 0.01 to about 0.2 mg of docusate sodium per ml of body fluid at the cellular level. For cutaneous and superficial bacterial infection, the preferred route of administration is by topical application of the docusate sodium as a spray, lotion, cream, salve, ointment or powder or the like. Preferably, the concentration of docusate sodium provided by the topical treatment is from about 0.01 to about 0.2 mg of docusate sodium per ml of fluid at the cellular level.

EXAMPLE 1

Topical Administration - Lotion

An exemplary embodiment of lotion prepared for topical administration for treating bacterial infection in accordance with practice of principles of this invention comprises 0.2% wt/wt docusate sodium, 5% wt/wt mineral oil, 4.5% wt/wt stearic acid, 3.5% wt/wt cetyl alcohol, 1.5% wt/wt triethanolamine, 0.15% wt/wt methylparaben, 0.05% wt/wt propylparaben with the remainder being deionized and filtered water.

The lotion is prepared in two phases, phase A which includes mineral oil, stearic acid, cetyl alcohol, and propylparaben and phase B which includes deionized and filtered water, triethanolamine, methylparaben and docusate sodium.

To prepare the lotion an appropriate amount of mineral oil is metered into a jacketed stainless steel vessel. Into the same vessel an appropriate amount of each of stearic acid, cetyl alcohol and propylparaben is measured. Moderate propeller agitation is provided and phase A (oil phase) is heated to 70° to 75° C. Mixing is continued until all solids are melted and a clear solution is obtained. Phase B is then obtained by weighing an appropriate amount of water into a jacketed stainless steel vessel (main mixing vessel) which is provided with both a propeller and a sweep agitation. Into the same vessel an appropriate amount of each of triethanolamine, methylparaben and docusate sodium is added. With gentle propeller agitation phase B is brought to 72°-77° C. to obtain a clear solution. Phase A is then added to phase B which is at 72°-77° C. with continued propeller agitation. Mixing is continued for 20 minutes with the combined phases at about 70° to about 77° C. The batch is then cooled by introducing cooling water into the jacket of the vessel. Cooling is continued with moderate propeller agitation. When the batch begins to thicken agitation is continued until batch temperature reaches about 25° C. to about 30° C. A sample is then taken from both the top and bottom of the batch for quality control analysis.

The product is then ready to be placed into containers for topical application.

A person who has acne infection (*Proprionibacterium acnes*) applies the lotion to the infected area of the skin periodically. In one embodiment the lotion is applied every 4 hours. The treatment is continued until the acne is healed.

While the above example illustrates the use of one exemplary lotion formulation, compositions are contemplated which included pharmaceutically acceptable carriers other than those of this embodiment. Additionally, the percentage of docusate sodium used can be different. For example, lotion formulations having as little as 0.001% to greater than 1% docusate sodium are contemplated.

EXAMPLE 2

Topical Administration - Cleanser

An exemplary embodiment of a cleanser prepared for topical administration for treating or preventing bacterial infection in accordance with practice of principles of this invention comprises 23.3% sodium ($C_{14}$-$C_{16}$) olefin sulfonate, 5% myristamine oxide, 1% cocamidopropylbetaine, 3.5% Lauramid DEA, 0.25% polyquaternium -7, 0.1% NaCl, 0.2% dioctyl sodium sulfosuccinate, a fragrance, a preservative with the remainder being water and containing sufficient citric acid to bring the pH of the cleanser to 7.

The cleanser is used to wash the external surface of the body for inactivating Gram positive bacteria on the surface which is contacted by the cleanser.

While the above Example illustrates the use of one exemplary cleanser formulation, formulations can be used which include pharmaceutically acceptable carriers other than those of this embodiment. Additionally, the percentage of docusate sodium used can be different. For example, cleanser formulations having as little as 0.001% to greater than 1% docusate sodium are contemplated.

EXAMPLE 3

Surface Sterilization

An exemplary embodiment of a sanitizer prepared for disinfecting surfaces such as bathroom and kitchen fixtures and the like in accordance with practice of principles of this invention comprises about 0.2% wt/wt docusate sodium, about 10.0% wt/wt ethanol and the remainder water.

The solution is sprayed onto a bathroom fixture, for example onto a toilet seat so that Gram positive bacteria on the toilet seat are inactivated.

While the above example illustrates the use of one exemplary sanitizer composition, compositions comprising other ingredients can be used. Additionally, the percentage of docusate sodium can be different. For example, sanitizers having as little as 0.001% to greater than 10% docusate sodium are contemplated.

EXAMPLE 4

Systemic Administration Time/Sustained-Release Capsule

In one exemplary embodiment of practice of this invention for systemic treatment of bacterial infection, docusate sodium is provided in a time/sustained-release capsule form as is known in the art. From about 5 mgs to about 35 gms of docusate sodium in such time/sustained-release capsule form is administered per day to a person who has a bacterial infection caused by *Streptococcus pyogenes*. The dosage administered is such that the systemic concentration of docusate sodium at the cellular level of the person being treated is from between 0.01 and 0.2 mg per ml.

EXAMPLE 5

Systemic Treatment - Tablet Form

In an exemplary embodiment of practice of this invention for systemic treatment, docusate sodium is administered in tablet form to a person, prior to and during his exposure to *Streptococcus pyogenes*, for preventing infection. The dosage is such that the systemic concentration of docusate sodium at the cellular level is maintained at from about 0.01 to 0.2 mg per ml.

EXAMPLE 6

Inactivating A Bacteria Using A Facial Tissue Impregnated With Docusate Sodium

A cellulosic web facial tissue is impregnated with an anti-bacterially effective amount of docusate sodium.

A person who has an infection caused by *Streptococcus pyogenes* uses the tissue for inhibiting *Streptococcus pyogenes*.

EXAMPLE 7

Use of Vaginal Tampon Impregnated with Docusate Sodium

A vaginal tampon is impregnated with an amount of docusate sodium effective to inhibit growth of *Staphylococcus aureus*. The tampon is inserted into the vagina.

The following experiments relate to in vitro tests to determine the effect of dioctyl sodium sulfosuccinate on various bacteria.

EXAMPLE 8

Effect of Dioctyl Sodium Sulfosuccinate On Gram Positive and Gram Negative Bacteria Trypticase soy broth (TSB) was sterilized by autoclaving. Filter sterilized dioctyl sodium sulfosuccinate in distilled water was added to the sterile broth to the final concentration shown in Table 1 below. The cultures were inoculated and incubated at 30° C. for 72 hours. Growth in the cultures was checked at 24 and 72 hours.

The results of this experiment are shown in Table 1.

TABLE 1

| Bacterial Species | mg/ml Compound II | | | | | | |
|---|---|---|---|---|---|---|---|
| | 0 | 2 | 1 | 0.5 | 0.25 | 0.125 | 0.06 |
| Growth at 24 Hours | | | | | | | |
| *Escherichia coli* | + | + | + | + | + | + | + |
| *Salmonella enteriditis* | + | + | + | + | + | + | + |
| *Pseudomonas aeroginosa* | + | + | + | + | + | + | + |
| *Enterobactor aerogenes* | + | + | + | + | + | + | + |
| *Streptococcus pyogenes* | + | − | − | − | − | − | + |
| *Staphylococcus aureus* | + | − | − | − | ± | + | + |
| Growth at 72 Hours | | | | | | | |
| *Escherichia coli* | + | + | + | + | + | + | + |
| *Salmonella enteriditis* | + | + | + | + | + | + | + |
| *Pseudomonas aeroginosa* | + | + | + | + | + | + | + |
| *Enterobactor aerogenes* | + | + | + | + | + | + | + |
| *Streptococcus pyogenes* | − | − | − | − | − | − | + |
| *Staphylococcus aureaus* | + | + | + | + | + | + | + |

+: Growth Present
−: Growth Absent

The results shown in Table 1 indicate that the Gram negative bacteria tested were not effected by dioctyl sodium sulfosuccinate under the experimental conditions used, whereas growth of the Gram positive organisms was inhibited or retarded. However, these results were qualitative since growth was recorded as present or absent rather than determined spectrophotometrically.

EXAMPLE 9

In this example the experiment of Example 8 was repeated with *Streptococcus pyogenes* and *Staphylococcus aureus* and the growth of the bacteria was measured spectrophotometrically at 540 nm. The results are shown in Table 2 below.

TABLE 2

| Bacterial Species | mg/ml dioctyl sodium sulfosuccinate | | | | | | |
|---|---|---|---|---|---|---|---|
| | 0 | 2 | 1 | 0.5 | 0.25 | 0.125 | 0.06 |
| Growth at 24 Hours | | | | | | | |
| *Staphylococcus aureus* | 1.0 | 0.04 | 0.19 | 0.23 | 0.20 | 0.39 | 0.85 |
| *Streptococcus pyogenes* | 0.9 | 0.04 | 0.05 | 0.06 | 0.13 | 0.10 | 0.8 |
| Growth at 48 Hours | | | | | | | |
| *Staphylococcus aureus* | 1.25 | 0.07 | 0.27 | 0.30 | 0.22 | 0.42 | 0.90 |
| *Streptococcus pyogenes* | 0.95 | 0.04 | 0.10 | 0.09 | 0.15 | 0.09 | 0.82 |
| Growth at 72 Hours | | | | | | | |
| *Staphylococcus aureus* | 1.25 | 0.18 | 0.34 | 0.47 | 0.22 | 0.48 | 0.90 |
| *Streptococcus pyogenes* | 0.95 | 0.03 | 0.26 | 0.12 | 0.15 | 0.02 | 0.80 |

Growth recorded as absorbance at 540 nm.

Table 2 shows the inhibitory effect of dioctyl sodium sulfosuccinate on growth of the test organisms both of which are Gram positive. It can be seen that at concentrations of dioctyl sodium sulfosuccinate which permit growth, the absorbance of the cultures did not reach the levels in the controls.

EXAMPLE 10

Effects of Prolonged Contact With Dioctyl Sodium Sulfosuccinate On Growth Of *Streptococcus pyogenes* And *Staphlococcus aureus*

The development of a resistance to dioctyl sodium sulfosuccinate by *Streptococcus pyogenes* and *Staphylococcus aureus* was evaluated. *Streptococcus pyogenes* and *Staphylococcus aureus* were grown in the presence of different concentrations of dioctyl sodium sulfosuccinate for 72 hours. After 72 hours a second set of cultures was inoculated using the first passage 2 mg/ml cultures as the inocula. Results of these experiments are shown in Table 3.

TABLE 3

| Bacterial Species | mg/ml dioctyl sodium sulfosuccinate | | | | | |
|---|---|---|---|---|---|---|
| | 0 | 2 | 1 | 0.5 | 0.25 | 0.125 | 0.06 |
| Growth at 72 Hours (1st Passage) | | | | | | |
| Staphylococcus aureus | 0.900 | 0.270 | 0.255 | 0.220 | 0.260 | 0.290 | 0.310 |
| Streptococcus pyogenes | 0.850 | 0.160 | 0.105 | 0.045 | 0.040 | 0.020 | 0.595 |
| Growth at 72 Hours (2nd Passage) | | | | | | |
| Staphylococcus aureus | 1.000 | 0.340 | 0.270 | 0.275 | 0.120 | 0.205 | 0.405 |
| Streptococcus pyogenes | 0.150 | 0.125 | 0.060 | 0.040 | 0.010 | 0.072 | 0.032 |

Growth recorded as absorbance at 540 nm.

The data in Table 3 indicate that the test organisms were less resistant to dioctyl sodium sulfosuccinate in the second passage than they were in the first passage. The results indicate that viability of the 72 hour first passage cultures was low which in turn suggested that dioctyl sodium sulfosccinate is bactericidal. To test this possibility viable cell count experiments were done.

EXAMPLE 11

Cultures containing different concentrations of dioctyl sodium sulfosuccinate were inoculated with *Streptococcus pyogenes* or *Staphylococcus aureus* and incubated for 72 hours. The cultures were transferred to a second set of culture media containing dioctyl sodium sulfosuccinate and incubated an additional 48 hours. The second passage cultures were serially diluted and viable cell counts determined in agar pour plates.

TABLE 4

| Incubation Time | Colony Counts/ml mg/ml dioctyl sodium sulfosuccinate | | |
|---|---|---|---|
| | 0 | 2 | 0.5 |
| *Streptococcus pyogenes* | | | |
| Initial | 12 × 10⁶ | 10 × 10⁴ | 10 × 10⁴ |
| 48 Hours | 88 × 10⁷ | 0 | 0 |
| *Staphylococcus aureus* | | | |
| Initial | 17 × 10⁶ | 6 × 10⁶ | 12 × 10⁶ |

TABLE 4-continued

| Incubation Time | Colony Counts/ml mg/ml dioctyl sodium sulfosuccinate | | |
|---|---|---|---|
| | 0 | 2 | 0.5 |
| 48 Hours | 18 × 10⁸ | 2.6 × 10⁶ | 7 × 10⁶ |

It can be seen that with both organisms the viable cell counts declined over the 48 hour incubation whereas the control counts increased. It appears from these results that in addition to being bacteriostatic, dioctyl sodium sulfosuccinate is a bactericide.

The above descriptions of exemplary embodiments of the methods and compositions for treating infections caused by Gram positive bacteria are for illustrative purposes. Because of variations, which will be apparent to those skilled in the art, the present invention is not intended to be limited to the particular embodiments described above. The scope of the invention is defined in the following claims.

What is claimed is:

1. A method for treating bacterial infections of humans caused by corynebacterium, the method comprising the steps of topically applying to a human infected with corynebacterium a pharmaceutically acceptable composition consisting essentially of an anti-bacterially effective amount of a compound of the following formula:

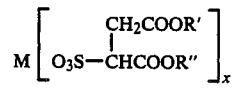

wherein R' and R" are each independently a straight chain or branched chain alkyl group having from 5 to 8 carbon atoms, M is Na, K or Ca, and x is 1 when M is Na or K, and x is 2 when M is Ca.

2. The method according to claim 1 wherein the anti-bacterial compound is dioctyl sodium sulfosuccinate.

3. The method according to claim 2 wherein the composition has a dioctyl sodium sulfosuccinate concentration of from about 0.01 to about 0.2 mg per ml of said composition.

4. The method according to claim 1 wherein the composition is applied at least daily during the course of the infection.

5. The method according to claim 1 wherein the composition is selected from the group consisting of a lotion, cream, salve, liquid, and dry power.

6. The method according to claim 1 wherein said corynebacterium is the species *Propionibacterium acnes*.

* * * * *